(12) United States Patent
Riera Giner et al.

(10) Patent No.: US 8,857,731 B2
(45) Date of Patent: Oct. 14, 2014

(54) VOLATILE SUBSTANCE EVAPORATOR WITH SUBSTANCE END-OF-LIFE DETECTOR

(75) Inventors: Montserrat Riera Giner, Barcelona (ES); Fernando Mayor Sans, Barcelona (ES); Cédric Morhain, Barcelona (ES); Ruben Garcia Fabrega, Barcelona (ES)

(73) Assignee: Zobele Espana, S.A., Barcelona (ES)

( * ) Notice: Subject to any disclaimer, the term of this patent is extended or adjusted under 35 U.S.C. 154(b) by 665 days.

(21) Appl. No.: 12/989,523

(22) PCT Filed: Apr. 22, 2009

(86) PCT No.: PCT/EP2009/054792
§ 371 (c)(1),
(2), (4) Date: Jul. 25, 2011

(87) PCT Pub. No.: WO2009/130235
PCT Pub. Date: Oct. 29, 2009

(65) Prior Publication Data
US 2011/0290905 A1   Dec. 1, 2011

(30) Foreign Application Priority Data
Apr. 24, 2008 (ES) .................................. 200801183

(51) Int. Cl.
| | |
|---|---|
| *A24F 25/00* | (2006.01) |
| *A61L 9/04* | (2006.01) |
| *B67D 7/08* | (2010.01) |
| *A61L 9/12* | (2006.01) |
| *A61L 9/03* | (2006.01) |
| *A01M 1/20* | (2006.01) |
| *G01F 23/292* | (2006.01) |

(52) U.S. Cl.
CPC ............... *G01F 23/292* (2013.01); *A61L 9/127* (2013.01); *A61L 9/037* (2013.01); *A01M 1/2077* (2013.01)

USPC .................. 239/35; 239/34; 239/44; 239/71; 239/74

(58) Field of Classification Search
USPC ................. 239/34, 35, 44, 43, 71, 72, 73, 74; 250/341.8
See application file for complete search history.

(56) References Cited

U.S. PATENT DOCUMENTS 5,268,145 A * 12/1993 Namba et al. ................. 422/425
6,069,354 A *  5/2000 Alfano et al. ................. 250/221

(Continued)

FOREIGN PATENT DOCUMENTS

| EP | 0 671 622 | 9/1995 |
|---|---|---|
| WO | 2006105382 | 10/2006 |
| WO | 2007138247 | 12/2007 |

OTHER PUBLICATIONS

Spanish Search Report and Written Opinion dated Aug. 5, 2010, from the corresponding Spanish Application.

(Continued)

*Primary Examiner* — Ryan Reis
(74) *Attorney, Agent, or Firm* — Katten Muchin Rosenman LLP

(57) ABSTRACT

The present invention generally relates to volatile substance evaporators having a container with wick, and has the object of providing a technique for effectively detecting end-of-life of the volatile substance housed within the container. The volatile substance evaporator is configured for coupling to, and maintaining in a stable position, a container of volatile substance having a wick with a lower end housed within said container and an upper end emerging from the container. The evaporator comprises an infrared light emitter disposed so as to emit a beam of light on said upper end of the wick, in such a manner that a receptor is disposed so as to capture said beam of light reflected by the upper end of the wick.

12 Claims, 3 Drawing Sheets

(56) References Cited

U.S. PATENT DOCUMENTS

| | | | |
|---|---|---|---|
| 7,164,849 B1 | 1/2007 | Bankers et al. | |
| 7,440,683 B2* | 10/2008 | Bankers et al. | 392/386 |
| 7,589,340 B2* | 9/2009 | Dancs et al. | 250/577 |
| 2005/0260764 A1 | 11/2005 | Grigsby, Jr. et al. | |
| 2006/0019962 A1 | 1/2006 | Makings et al. | |
| 2006/0181416 A1* | 8/2006 | Chen | 340/545.2 |
| 2006/0219962 A1* | 10/2006 | Dancs et al. | 250/577 |
| 2007/0058955 A1* | 3/2007 | Bankers et al. | 392/386 |

OTHER PUBLICATIONS

International Search Report dated Sep. 29, 2009 for corresponding International Patent Application PCT/EP2009/054792.

Written Opinion of the International Searching Authority dated Sep. 29, 2009, from corresponding International Application No. PCT/EP2009/054792.

* cited by examiner

VOLATILE SUBSTANCE EVAPORATOR WITH SUBSTANCE END-OF-LIFE DETECTOR

This application is the National Stage of International Application No. PCT/EP2009/054792, filed Apr. 22, 2009, which claims the benefit under 35 U.S.C. 119 (a-e) of P200801183 filed Apr. 24, 2008, which is herein incorporated by reference.

OBJECT OF THE INVENTION

The present invention generally relates to volatile substance evaporators having a container with a wick, and has the object of providing an effective technique for detecting end-of-life of the volatile substance housed within the container.

BACKGROUND OF THE INVENTION

In volatile substance diffuser devices with wick, there is a need to allow the user to easily detect end-of-life of the volatile substance and therefore perceive the need to replace the container of the substance with a new one. These devices are generally plugged into out-of-sight household power outlets, due to which the level of liquid remaining in the container is not easily seen at first sight.

There are several solutions for converting end-of-life into an electric indicator that can then imply some type of alert to the user. These systems are based on the measurement of a change in physical properties, such as electrical conductivity, dielectric capacity, weight, temperature or light interaction.

With regard to the light interaction-based liquid detection systems, we can differentiate between detection systems for detecting liquid at the bottom of the container or inside the wick.

Detection systems for detecting liquid at the bottom of the container, for example, by means of light transmission, have the following drawbacks:

High degree of dispersion due to the lack of geometric accuracy of the bottles generally used.

Influence of external conditions (sunlight, reflections, . . . ).

End-of-life is detected when there is still liquid inside the wick and due to which evaporation of the formulation still occurs.

On the other hand, there are systems based on light transmission or refraction through the upper part of the wick. However, these systems require the wick to be transparent to light or that, in the presence of liquid inside the wick, a sufficient amount of light can be refracted through the cavities of the wick and reach the sensor.

These systems have the following drawbacks:

Need to adjust the position of the light emitter/sensor based on the refractive index of the fragrance.

Influence of external conditions (sunlight, reflections, . . . ).

U.S. Pat. No. 7,164,849 describes a device wherein the vaporisable liquid includes an IR-absorbing material. When there is sufficient vaporisable material in the container, the infrared light emitted cannot be reflected by the material towards the IR sensor. The infrared light is absorbed by the vaporisable material in such a manner that the IR sensor does not detect the IR light. When the IR sensor detects IR light the alarm is activated.

In North American patent application US 2006019962 A1, the light emitter and receptor may be disposed in any position of the diffuser around the wick and provided that the emitter and receptor are aligned facing each other. When the container is full or contains a certain amount of liquid, the wick absorbs the liquid. In this case, when there is liquid remaining in the container and the wick is wet, the light emitted by the emitter is refracted through the saturated porous wick, allowing the light to be detected by the sensor.

The refractive index of the liquid and the wick material determine the amount of light emitted by the emitter that is detected by the receptor. For example, as the refractive index of water is very low, the light emitted by the emitter is not refracted through the wick. Therefore, the refractive index of the liquid must be sufficiently high so as to refract the light through the wick and ensure that the light will be detected by the sensor.

In an alternative option, the emitter and light detector may be disposed on the container. One is disposed on the upper part and the other on the lower part of the container. When the container is empty, the light may pass through it. However, when there is liquid the light is refracted or reflected and does not reach the sensor.

In another option, the emitter and receptor are disposed around the container but not aligned. When there is liquid the light is scattered through the container and reaches the receptor, but when there is no liquid the light travels in a straight line and does not reach the receptor. It detects when the container is completely empty or almost empty, depending on the position of the sensor.

The drawbacks of these systems are the following:

Light transmission through the wick is not very efficient and requires a high-sensitivity sensor.

In order for light transmission to be sufficiently efficient, specific wick characteristics are required (pore size, pore percentage, . . . ).

Possible interference by ambient light.

The light emitter and sensor must be aligned facing each other, which entails technical difficulties for reducing position tolerances.

On the other hand, international application WO2007/138247 describes an end-of-life detection system based on two methods:

Use of light refraction through the glass container.

Use of total internal reflection (combination of refraction and reflection).

The light source is adapted to direct IR or visible light towards the container at an angle that is substantially within or between:

a) a critical angle of incidence for an interphase between the liquid and the container; and b) a critical angle of incidence due to an interphase between the air and the container.

The critical angle is preferably a critical angle for total internal reflection. The sensor is disposed in such a manner as to receive light from the emitting source that has entered the container and has been reflected in the interphase between the container and the air inside the container. Or, to receive light from the light source that has entered the container and has been refracted in the interphase between the container and the air. The sensor must be disposed in relation to the light source in such a manner that the liquid of the container is present at detection level. The emitter and detector must be in the line of sight.

The drawbacks of this system are the following:

It requires an adequate positioning of the emitter so that the light enters the container at certain angles.

The container must be made of glass. The emitter/receptor system depends on the thickness and purity of the glass.

The container and emitter/receptor system must be designed in such a manner that the wick does not interfere with the light path.

In the total internal reflection method there will always be fragrance remaining in the container and an additional end-of-life indication system is required (timer, . . . ).

DESCRIPTION OF THE INVENTION

The present invention relates to a volatile substance evaporator device having means to detect end-of-life of the substance to be evaporated. The evaporator is configured for coupling to, and maintaining in a stable position, a container with a volatile substance having a porous wick partially immersed in the substance container and with an upper end emerging from the container.

By wick we understand any type of adequate capillary medium for correctly transporting liquid from the container to the evaporation zone. Ceramic or fibre wicks having cylindrical geometry are the most common embodiments. But the wick may also have a flat geometry. Even capillary channels machined into the wall of a non-porous solid support are susceptible to being used as wicks in the present invention.

The evaporator comprises an infrared light and emitter and receptor, where the emitter is disposed so as to emit a beam of light on the end or upper part of the wick, and the receptor is disposed so as to capture said beam of light reflected by the upper part of the wick. Detection therefore occurs through the reflection of a beam of IR light on the outer surface of the upper portion of the wick.

The device is coupled to the aforementioned container of volatile substances equipped with the porous wick. The volatile substance housed in the container includes an additive or mixture of infrared (IR) light-absorbing additives, as a component of the formulation of a volatile solution to be evaporated in an evaporating device.

The solution with the IR absorber soaks the wick up to the upper part thereof, where it receives a beam of IR light from the emitter which is reflected on the wick if dry or absorbed by the wick if soaked with the absorbing liquid. The presence or absence of a reflected beam is detected by an IR sensor adequately disposed so as to receive the reflected beam.

A pigment or combination of pigments that allow the minimisation of the IR light within the range of 800 nm to 2000 nm (near IR) is preferably used. Likewise, it is adequate to minimise the absorption of the visible light of the absorbing pigment within the range of 450 nm to 800 nm.

The IR emitter is selected so as to produce maximum emission in the wavelength where the absorptivity of the IR-absorbing additive is maximum. The wavelength range is preferably between 800 nm and 1500 nm. Additionally, the angle of view of the IR emitter must be equal to or less than 40° in order to avoid false detection.

DESCRIPTION OF THE DRAWINGS

For the purpose of complementing this description and helping to better understand the characteristics of the invention, in accordance with a preferred example of practical embodiment thereof, a set of drawings has been included as an integral part of this description, wherein the following figures have been represented in an illustrative and non-limitative manner.

PREFERRED EMBODIMENT OF THE INVENTION

Figure 1C:
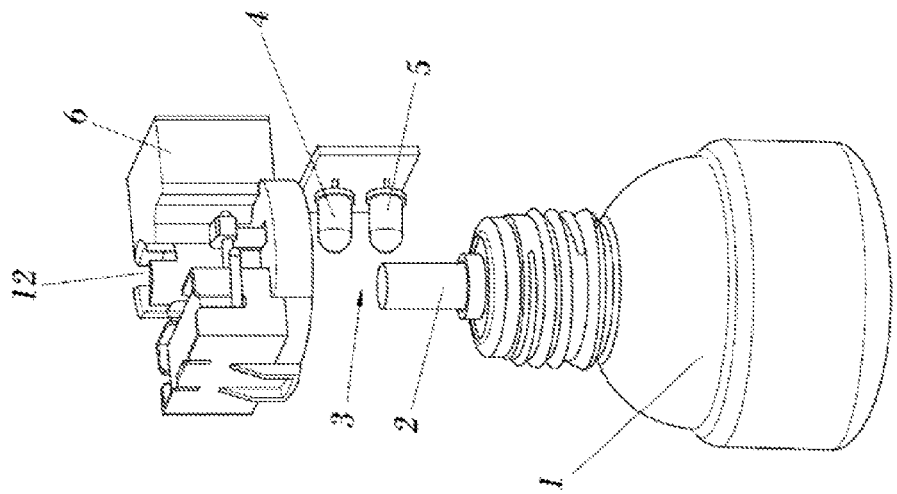
FIG. 1 shows in an uncoupled position: the container with wick, the infrared emitter/receptor and part of the evaporator. Figure (a) is a side view, figure (b) is a front view and figure (c) is a perspective view.
Figure 1B:
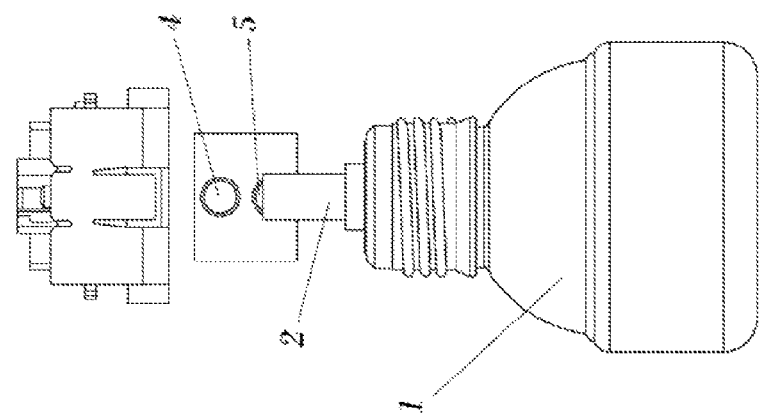
Figure 1A:
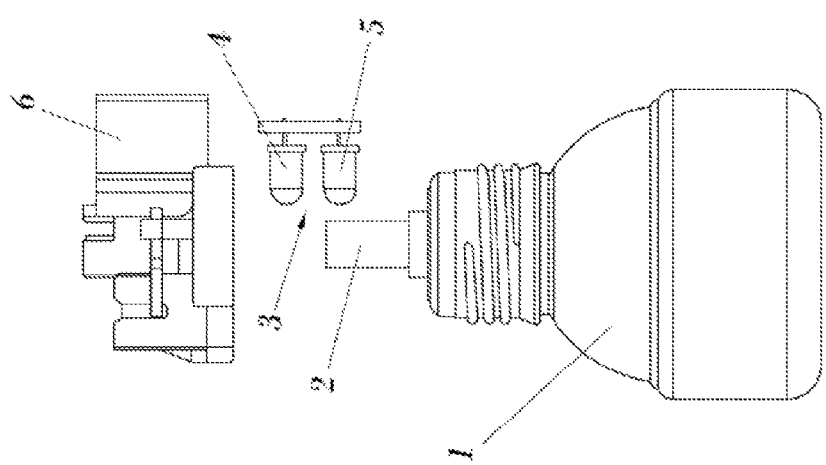

FIG. 1 represents a container (1) conventionally equipped with a porous wick (2) having a lower end (9) within the container and immersed in the liquid to be evaporated (10). An upper end (8) of the wick (2) emerges from the container to allow the diffusion of the volatised substance into the air.

For the purpose of simplifying the figures, we have represented a single component of the evaporator (6), consisting of a casing that houses heating means (7) (traditionally a PTC resistor) and having a cavity (12) within which the upper end (8) of the wick is positioned when the evaporator and container are coupled together. This same component of the evaporator (6) also houses means for detecting the presence of a volatile substance (3), consisting of an infrared emitter (4) and an infrared receptor (5).

As it is already known in the state of the art, the evaporator and container are configured to remain coupled together, for example threaded, during normal use of the device, maintaining the wick in a stable position. In this preferred embodiment, and as can be observed especially in FIG. 2(d), the upper end (8) of the wick is housed within the cavity (12) and is disposed, on one side, next to the heating means (7) and, on the other, to the detection means.

The emitter and receptor (4, 5) overlap each other at a certain distance and in such a manner as to face each other on the same side of the upper end of the wick. During use of the device and in the presence of a volatile substance, the total wick volume becomes fully impregnated with said substance, which contains a fraction of pigment or combination of IR-absorbing pigments.

The emitter (4) continuously emits a beam of infrared light that incides on the outer surface of the upper part (8) of the wick. Alternatively, said beam of infrared light is emitted by pulses with the object of lengthening the useful life of the emitter and receptor.

Said beam is absorbed by the IR-absorbing pigment, due to which it is not reflected and does not reach the IR receptor. However, when all or most of the volatile substance in the upper part of the wick has been consumed, the beam of infrared light is reflected on the upper part of the wick and reaches the receptor (5) that detects the presence of the beam of IR light, indicating end-of-life of the volatile substance.

The IR receptor typically consists of an IR-sensitive phototransistor that may be used in the manner known to a person skilled in the art, to activate a indicator element (not represented), such as for example a LED or an acoustic indicator that alerts the user on substance end-of-life.

The emitter and receptor form an adequate angle in order to guarantee correct detection, and are very close to the outer wick surface.

The IR light emitter and receptor are disposed in such a manner that their axes are parallel and in turn perpendicular to each other with respect to the longitudinal axis of the wick, as shown in FIG. 2.

Figure 3:
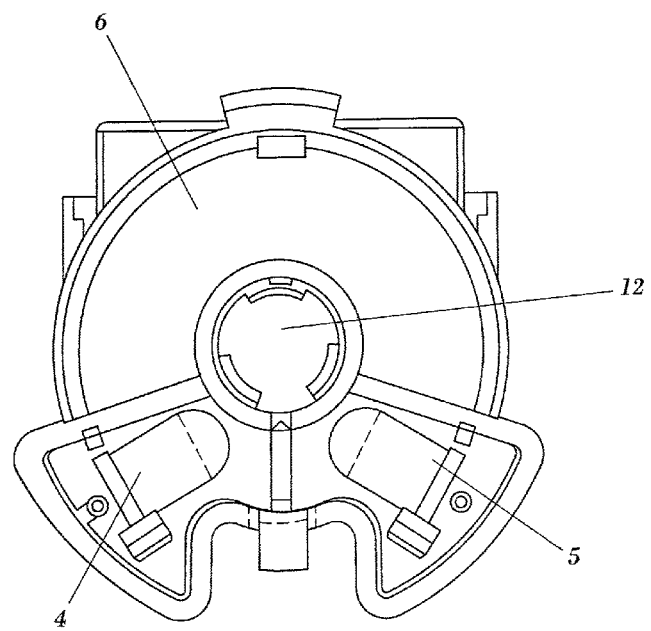
FIG. 3 shows an upper plan view of a preferred embodiment of the invention wherein the emitter and receptor are within the same plane at an angle to each other.

In another example of embodiment represented in FIG. 3, the axes of the emitter and receptor form an angle between each other in such a manner that the receptor captures the IR light reflected on the wick.

These arrangements of the emitter and receptor with respect to the wick allow the detection to occur through the reflection of the IR light beam instead of refraction or transmission, as in the techniques known in the state of the art. In this manner, the aforementioned drawbacks of the known systems are avoided.

In a preferred embodiment of the invention, the liquid contained inside the bottle is biphasic in nature and is composed of an aqueous phase (water) and an organic phase (fragrance). The IR-absorbing additive may be integrated in the aqueous phase or organic phase. The aqueous phase reaches the wick only when the organic phase (fragrance, insecticide, ...) is depleted. Therefore, when the IR-absorbing additive is in the aqueous phase, while there is still organic phase in the wick the beam of IR light is reflected by the wick. When the organic phase becomes depleted, the aqueous liquid can reach the upper part and absorb the IR light. In this case, detection of substance end-of-life occurs when the IR receptor no longer detects the presence of the beam of IR light in the receptor.

In the opposite case, i.e. when the IR-absorbing additive is in the organic phase, detection of end-of-life of the organic phase occurs when the aqueous phase reaches the upper part of the wick and reflects the IR light, the reflection of which reaches the receptor.

Figure 2A:
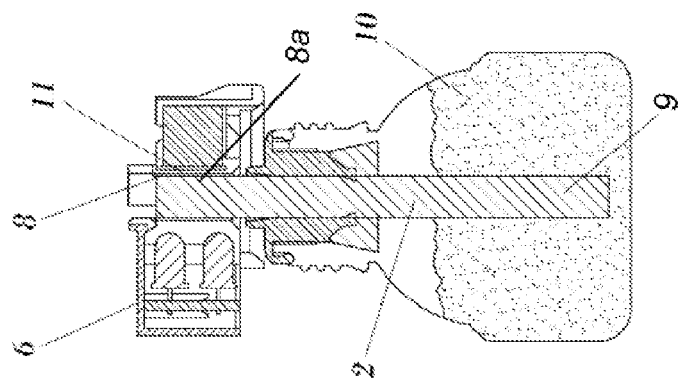
FIG. 2 shows a similar representation to the preceding figure, where the container with wick, the infrared emitter/receptor and part of the evaporator are coupled together in the normal use position. Figure (a) is a perspective view, figure (b) is a front view, figure (c) is a side view and figure (d) is a sectional side view.
Figure 2B:
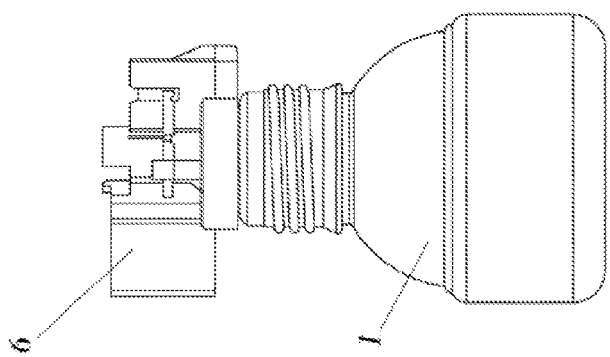
Figure 2C:
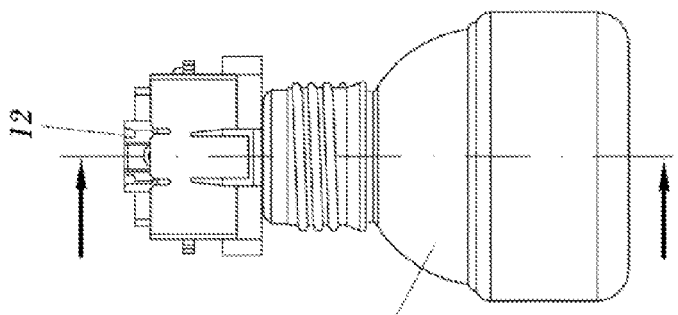
Figure 2D:
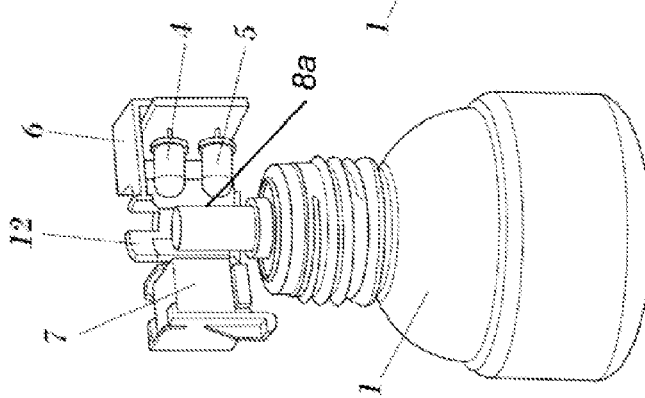

Preferably, the evaporator has a surface (8a) with known IR-absorbing/reflecting properties (11) disposed diametrically opposite to said emitter and receptor (4, 5). The upper part of the wick (8) is interposed between said surface (11) and the emitter and receptor, as shown in FIG. 2(d). Therefore, the specific location of the emitter and receptor provides the additional advantage that the absence of a container coupled to the device can be detected and therefore the user can be alerted of said circumstance.

In the case of embodiments where end-of-life is detected by the non-reflection of infrared light, the surface (11) will be made of a non-IR light reflecting material. Under such circumstances the IR lights incides directly on the surface of an absorbent material (11), in such a manner that the presence of the reflected beam is not detected by the adequately disposed IR sensor, which will activate the indicator means.

Diverse possibilities of practical embodiments of the invention are described in the attached dependent claims.

According to this description and set of drawings, a person skilled in the art will be capable of understanding that the described embodiments of the invention may be combined in multiple manners within the object of the invention. The invention has been described according to some preferred embodiments thereof, but for a person skilled in the art it will be evident that multiple variations may be introduced in said preferred embodiments without exceeding the object of the invention being claimed.

The invention claimed is:

1. A volatile substance evaporator indicating an end-of-life condition of the volatile substance, the evaporator comprising:
    a volatile substance comprising an infrared light absorbing additive;
    a container holding the volatile substance;
    a wick having a lower part and an upper part, the lower part disposed inside the container and the upper part disposed outside of the container, the wick wicking the volatile substance from the lower part to the upper part, the upper part comprising an infrared light reflecting material;
    an infrared light emitter for emitting infrared light onto the upper part,
    a receptor for detecting the infrared light reflected from the upper part;
    wherein the upper part reflects the infrared light relative to an amount of the volatile substance present in the upper part;
    wherein the receptor determines an end-of-life condition of the volatile substance based on a pre-determined amount of infrared light detected.

2. The volatile substance evaporator of claim 1, wherein the volatile substance comprises a high infrared light-absorbing coefficient.

3. The volatile substance evaporator of claim 1, wherein the wick comprises a first axis, the emitter comprises a second axis, and the receptor comprises a third axis, the third axis being substantially perpendicular to the first axis and being substantially parallel to the second axis.

4. The volatile substance evaporator of claim 1, wherein the wick comprises a first axis, the emitter comprises a second axis, and the receptor comprises a third axis, the second axis and third axis being disposed in one plane, the plane being substantially perpendicular to the first axis.

5. The volatile substance evaporator of claim 1, wherein the emitter emits the infrared light in pulses.

6. The volatile substance evaporator of claim 1, wherein the volatile substance comprises an organic phase and an aqueous phase, the organic phase comprising the infrared light absorbing additive.

7. The volatile substance evaporator of claim 1, wherein the volatile substance comprises an organic phase and an aqueous phase, the aqueous phase comprising the infrared light absorbing additive.

8. The volatile substance evaporator of claim 1, wherein the infrared light comprises a wavelength between 800 nm and 1500 nm.

9. The volatile substance evaporator of claim 1, further comprising a first surface comprising an infrared light-reflecting material, the upper end of the wick being disposed between the first surface and the emitter and between the first surface and the receptor.

10. The volatile substance evaporator of claim 1, further comprising an indicator indicating the end-of-life condition of the volatile substance, the indicator being responsive to the receptor.

11. The volatile substance evaporator of claim 1, further comprising a first surface comprising a material that does not reflect infrared light, the upper end of the wick being disposed between the first surface and the emitter and between the first surface and the receptor.

12. The volatile substance evaporator of claim 1, further comprising an indicator indicating the end-of-life condition of the volatile substance, the indicator being responsive to the receptor when the receptor no longer receives infrared light.

* * * * *